United States Patent [19]

Honjo et al.

[11] Patent Number: 5,496,713
[45] Date of Patent: Mar. 5, 1996

[54] PROCESS FOR PRODUCING 20 KD HUMAN GROWTH HORMONE

[75] Inventors: Masaru Honjo, Chiba; Setsuo Yoshino, Fukuoka; Akira Nakayama; Naokazu Naito, both of Chiba, all of Japan

[73] Assignee: Mitsui Toatsu Chemicals, Inc., Tokyo, Japan

[21] Appl. No.: 117,809

[22] Filed: Sep. 9, 1993

[30] Foreign Application Priority Data

Sep. 9, 1992 [JP] Japan .................................. 4-240936
Jan. 25, 1993 [JP] Japan .................................. 5-009911

[51] Int. Cl.$^6$ ........................... C12P 21/06; C12N 15/24; A61K 38/27; C07K 14/61
[52] U.S. Cl. ....................... 435/69.4; 435/69.8; 435/71.2; 435/320.1; 530/399
[58] Field of Search ................................. 435/69.4, 69.8; 530/399

[56] References Cited

FOREIGN PATENT DOCUMENTS

| | | |
|---|---|---|
| 61-151015 | 7/1986 | Japan . |
| 61-224988 | 10/1986 | Japan . |
| 1-273591 | 11/1989 | Japan . |
| WO88/10299 | 12/1988 | WIPO . |

OTHER PUBLICATIONS

Honjo et al. 1986 J Biotechnology 4:63–71.
Nakayama et al. 1987 J Biotechnology 6:171–179.
Honjo et al 1987 J Biotechnology 6:191–204.
Sambrook et al 1989 Molecular Cloning A Lab. Manual. CSHL Press, CSH, NY. Excepts Chapter 17 & Appendix.
Journal of Biotechnology, vol. 8, 1988, pp. 123–134, Makayama.
Gene, vol. 55, 1987, pp. 189–196.
Rogers et al, The Lancet, Aug. 27, 1977, pp. 434–435.
Fisher et al, The Lancet, May 21, 1988, pp. 1159–1160.
Horumon to Rinsho, vol. 38, 1990, pp. 155–159 (and translation of pertinent portions).
Endocrinol, Japon, vol. 36, 1989, pp. 9–13.
Endocrinol, Japon. vol. 34, 1987, pp. 73–85, Lewis.
Int'l. Symposium on GRF, Growth Hormone & Somatomedin Program & abstracts, 28, Nov. 1–2, 1986.
Gene, vol. 39, 1985, pp. 247–254.
J. Cell Biology, vol. 67, 1975, pp. 835–851.
Biochimica et Biophysica Acta, vol. 949 (1988), pp. 125–131.
Science, vol. 205, Aug. 10, 1979, pp. 602–607.
Trends in Biotech., vol. 10, 1992, pp. 310–315.
J. Biol. Chem., vol. 241, No. 13, Jul. 10, 1966, pp. 3055–3062.
Nucleic Acids Research, vol. 5, No. 7, Jul. 1978, pp. 2321–2332.
Journal of Immunology, vol. 116, No. 6, Jun. 1976, pp. 1554–1560.
Journal of Biol. Chemistry, vol. 255, No. 1, Jan. 1980, pp. 27–29.
Journal of Biotechnology, vol. 8, 1988, pp. 123–134.

*Primary Examiner*—Garnette D. Draper
*Assistant Examiner*—K. Cochrane Carlson
*Attorney, Agent, or Firm*—Burns, Doane, Swecker & Mathis

[57] ABSTRACT

A human growth hormone having a molecular weight of 20,000 daltons can be effectively secreted and produced in the periplasm of *Escherichia coli* by constructing a human growth hormone secretion plasmid comprising a vector DNA replicable in *E. coli* and a DNA fragment including a promoter, a ribosome binding site, a secretion signal coding region, which are all those of the neutral protease gene of *B. amyloliquefaciens* and a gene encoding 20 kD hGH placed just downstream from the secretion signal coding region; introducing the said plasmid into *E. coli*; and culturing the resultant transformed cells.

4 Claims, 1 Drawing Sheet

FIG. 1

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 859 base pairs
        ( B ) TYPE: nucleic acid
        ( C ) STRANDEDNESS: double
        ( D ) TOPOLOGY: linear     ( i i ) MOLECULE TYPE: DNA (genomic)

( v i ) ORIGINAL SOURCE:
        ( A ) ORGANISM: Bacillus amyloliquefaciens
        ( B ) STRAIN: MT-272

( i x ) FEATURE:
        ( A ) NAME/KEY: CDS
        ( B ) LOCATION: 251..859

( i x ) FEATURE:
        ( A ) NAME/KEY: misc_feature
        ( B ) LOCATION: 179..208
        ( D ) OTHER INFORMATION: /note="Nucleotides 179-208 are S
            promoter."

( i x ) FEATURE:
        ( A ) NAME/KEY: sig_peptide
        ( B ) LOCATION: 251..331

( i x ) FEATURE:
        ( A ) NAME/KEY: RBS
        ( B ) LOCATION: 236..242

( i x ) FEATURE:
        ( A ) NAME/KEY: mat_peptide
        ( B ) LOCATION: 332..859

( x i ) SEQUENCE DESCRIPTION: SEQ ID NO:1:

```
GATCTTAACA  TTTTTCCCCT  ATCATTTTTC  CCGTCTTCAT  TTGTCATTTT  TTCCAGAAAA          60

AATCGTCATT  CGACTCATGT  CTAATCCAAC  ACGTCTCTCT  CGGCTTATCC  CCTGACACCG         120

CCCGCCGACA  GCCCGCATGG  ACGAATCTAT  CAATTCAGCC  GCGGAGTCTA  GTTTTATATT         180

GCAGAATGCG  AGATTGCTGG  TTTATTATAA  CAATATAAGT  TTTCATTATT  TTCAAAAAGG         240

GGGATTTATT  GTG GGT TTA GGT AAG AAA TTG TCT AGT GCT GTA GCC GCT                289
            Met Gly Leu Gly Lys Lys Leu Ser Ser Ala Val Ala Ala
                -25                 -20                 -15

TCC TTT ATG AGT TTA ACC ATC AGT CTG CCG GGT GTT CAG GCC TTC CCA                337
Ser Phe Met Ser Leu Thr Ile Ser Leu Pro Gly Val Gln Ala Phe Pro
            -10                 -5                  1

ACT ATA CCA CTT TCG CGC CTA TTC GAT AAC GCA AGT CTA CGT GCT CAC                385
Thr Ile Pro Leu Ser Arg Leu Phe Asp Asn Ala Ser Leu Arg Ala His
        5               10                  15

CGA CTA CAT CAG CTG GCC TTT GAC ACC TAC CAG GAG TTT AAC CCC CAG                433
Arg Leu His Gln Leu Ala Phe Asp Thr Tyr Gln Glu Phe Asn Pro Gln
    20              25                  30

ACC TCC CTC TGT TTC TCA GAG TCT ATT CCG ACA CCC TCC AAC AGG GAG                481
Thr Ser Leu Cys Phe Ser Glu Ser Ile Pro Thr Pro Ser Asn Arg Glu
35              40                  45              50

GAA ACA CAA CAG AAA TCC AAC CTA GAG CTG CTC CGC ATC TCC CTG CTG                529
Glu Thr Gln Gln Lys Ser Asn Leu Glu Leu Leu Arg Ile Ser Leu Leu
            55                  60                  65

CTC ATC CAG TCG TGG CTG GAG CCC GTG CAG TTC CTC AGG AGT GTC TTC                577
Leu Ile Gln Ser Trp Leu Glu Pro Val Gln Phe Leu Arg Ser Val Phe
```

|  |  |  |  |  |  |  |  |  |  |  |  |  |  |  |  |
|---|---|---|---|---|---|---|---|---|---|---|---|---|---|---|---|
|  |  | 70 |  |  |  |  | 75 |  |  |  |  | 80 |  |  |  |
| GCC | AAC | AGC | CTG | GTG | TAC | GGC | GCC | TCT | GAC | AGC | AAC | GTC | TAT | GAC | CTC | 625 |
| Ala | Asn | Ser | Leu | Val | Tyr | Gly | Ala | Ser | Asp | Ser | Asn | Val | Tyr | Asp | Leu |
|  |  | 85 |  |  |  |  | 90 |  |  |  |  | 95 |  |  |  |
| CTA | AAG | GAC | CTA | GAG | GAA | GGC | ATC | CAA | ACG | CTG | ATG | GGG | AGG | CTG | GAA | 673 |
| Leu | Lys | Asp | Leu | Glu | Glu | Gly | Ile | Gln | Thr | Leu | Met | Gly | Arg | Leu | Glu |
|  | 100 |  |  |  | 105 |  |  |  |  | 110 |  |  |  |  |  |
| GAT | GGC | AGC | CCC | CGG | ACT | GGG | CAG | ATC | TTC | AAG | CAG | ACC | TAC | AGC | AAG | 721 |
| Asp | Gly | Ser | Pro | Arg | Thr | Gly | Gln | Ile | Phe | Lys | Gln | Thr | Tyr | Ser | Lys |
| 115 |  |  |  | 120 |  |  |  |  | 125 |  |  |  |  | 130 |  |
| TTC | GAC | ACA | AAC | TCA | CAC | AAC | GAT | GAC | GCA | CTA | CTC | AAG | AAC | TAC | GGG | 769 |
| Phe | Asp | Thr | Asn | Ser | His | Asn | Asp | Asp | Ala | Leu | Leu | Lys | Asn | Tyr | Gly |
|  |  |  |  | 135 |  |  |  |  | 140 |  |  |  |  | 145 |  |
| CTG | CTC | TAC | TGC | TTC | AGG | AAG | GAC | ATG | GAC | AAG | GTC | GAG | ACA | TTC | CTG | 817 |
| Leu | Leu | Tyr | Cys | Phe | Arg | Lys | Asp | Met | Asp | Lys | Val | Glu | Thr | Phe | Leu |
|  |  |  | 150 |  |  |  |  | 155 |  |  |  |  | 160 |  |  |
| CGC | ATC | GTG | CAG | TGC | CGC | TCT | GTG | GAG | GGC | AGC | TGT | GGC | TTC |  |  | 859 |
| Arg | Ile | Val | Gln | Cys | Arg | Ser | Val | Glu | Gly | Ser | Cys | Gly | Phe |
|  |  | 165 |  |  |  |  | 170 |  |  |  |  | 175 |  |  |  |

( 2 ) INFORMATION FOR SEQ ID NO:2:

( i ) SEQUENCE CHARACTERISTICS:
        ( A ) LENGTH: 859 base pairs
        ( B ) TYPE: nucleic acid
        ( C ) STRANDEDNESS: double
        ( D ) TOPOLOGY: linear     ( i i ) MOLECULE TYPE: DNA (genomic)

( v i ) ORIGINAL SOURCE:
        ( A ) ORGANISM: Bacillus amyloliquefaciens
        ( B ) STRAIN: MT-272

( i x ) FEATURE:
        ( A ) NAME/KEY: misc_feature
        ( B ) LOCATION: 179..208
        ( D ) OTHER INFORMATION: /note="Nucleotides 179-208 are S
            promoter."

( i x ) FEATURE:
        ( A ) NAME/KEY: CDS
        ( B ) LOCATION: 251..859

( i x ) FEATURE:
        ( A ) NAME/KEY: RBS
        ( B ) LOCATION: 236..242

( i x ) FEATURE:
        ( A ) NAME/KEY: sig_peptide
        ( B ) LOCATION: 251..331

( i x ) FEATURE:
        ( A ) NAME/KEY: mat_peptide
        ( B ) LOCATION: 332..859

( x i ) SEQUENCE DESCRIPTION: SEQ ID NO:2:

| GATCTTAACA | TTTTTCCCCT | ATCATTTTC | CCGTCTTCAT | TTGTCATTTT | TTCCAGAAAA | 60 |
|---|---|---|---|---|---|---|
| AATCGTCATT | CGACTCATGT | CTAATCCAAC | ACGTCTCTCT | CGGCTTATCC | CCTGACACCG | 120 |
| CCCGCCGACA | GCCCGCATGG | ACGAATCTAT | CAATTCAGCC | GCGGAGTCTA | GTTTTATATT | 180 |
| GCAGAATGCG | AGATTGCTGG | TTTATTATAA | CAATATAAGT | TTTCATTATT | TTCAAAAAGG | 240 |

|  |  |  |  |  |  |  |  |  |  |  |  |  |
|---|---|---|---|---|---|---|---|---|---|---|---|---|
| GGGATTTATT | GTG | GGT | TTA | GGT | AAG | AAA | TTG | TCT | AGT | GCT | GTA | GCC | GCT | 289 |
|  | Met | Gly | Leu | Gly | Lys | Lys | Leu | Ser | Ser | Ala | Val | Ala | Ala |
|  | -25 |  |  |  | -20 |  |  |  |  | -15 |  |  |  |
| TCC | TTT | ATG | AGT | TTA | ACC | ATC | AGT | CTG | CCG | GGT | GTT | CAG | GCC | TTC | CCA | 337 |
| Ser | Phe | Met | Ser | Leu | Thr | Ile | Ser | Leu | Pro | Gly | Val | Gln | Ala | Phe | Pro |
|  |  | -10 |  |  |  | -5 |  |  |  |  |  |  |  |  | 1 |

```
ACT ATA CCA CTT TCG CGC CTA TTC GAT AAC GCA ATG CTA CGT GCT CAC    385
Thr Ile Pro Leu Ser Arg Leu Phe Asp Asn Ala Met Leu Arg Ala His
         5               10                  15

CGA CTA CAT CAG CTG GCC TTT GAC ACC TAC CAG GAG TTT AAC CCC CAG    433
Arg Leu His Gln Leu Ala Phe Asp Thr Tyr Gln Glu Phe Asn Pro Gln
     20              25                  30

ACC TCC CTC TGT TTC TCA GAG TCT ATT CCG ACA CCC TCC AAC AGG GAG    481
Thr Ser Leu Cys Phe Ser Glu Ser Ile Pro Thr Pro Ser Asn Arg Glu
 35              40                  45                      50

GAA ACA CAA CAG AAA TCC AAC CTA GAG CTG CTC CGC ATC TCC CTG CTG    529
Glu Thr Gln Gln Lys Ser Asn Leu Glu Leu Leu Arg Ile Ser Leu Leu
             55                  60                  65

CTC ATC CAG TCG TGG CTG GAG CCC GTG CAG TTC CTC AGG AGT GTC TTC    577
Leu Ile Gln Ser Trp Leu Glu Pro Val Gln Phe Leu Arg Ser Val Phe
             70                  75                  80

GCC AAC AGC CTG GTG TAC GGC GCC TCT GAC AGC AAC GTC TAT GAC CTC    625
Ala Asn Ser Leu Val Tyr Gly Ala Ser Asp Ser Asn Val Tyr Asp Leu
         85                  90                  95

CTA AAG GAC CTA GAG GAA GGC ATC CAA ACG CTG ATG GGG AGG CTG GAA    673
Leu Lys Asp Leu Glu Glu Gly Ile Gln Thr Leu Met Gly Arg Leu Glu
     100                 105                 110

GAT GGC AGC CCC CGG ACT GGG CAG ATC TTC AAG CAG ACC TAC AGC AAG    721
Asp Gly Ser Pro Arg Thr Gly Gln Ile Phe Lys Gln Thr Tyr Ser Lys
115             120                 125                     130

TTC GAC ACA AAC TCA CAC AAC GAT GAC GCA CTA CTC AAG AAC TAC GGG    769
Phe Asp Thr Asn Ser His Asn Asp Asp Ala Leu Leu Lys Asn Tyr Gly
                 135                 140                 145

CTG CTC TAC TGC TTC AGG AAG GAC ATG GAC AAG GTC GAG ACA TTC CTG    817
Leu Leu Tyr Cys Phe Arg Lys Asp Met Asp Lys Val Glu Thr Phe Leu
             150                 155                 160

CGC ATC GTG CAG TGC CGC TCT GTG GAG GGC AGC TGT GGC TTC            859
Arg Ile Val Gln Cys Arg Ser Val Glu Gly Ser Cys Gly Phe
         165                 170                 175
```

PROCESS FOR PRODUCING 20 KD HUMAN GROWTH HORMONE

BACKGROUND OF THE INVENTION

1. Field of the Invention

The present invention relates to a process for the production of a human growth hormone, more specifically to a human growth hormone secretion plasmid which allows the secretion and accumulation of a human growth hormone having a molecular weight of 20,000 (hereinafter referred to as 20 kD hGH) into the periplasm of *Escherichia coli*, and to a process for the production of the human growth hormone using a transformed strain of *E. coli* in which the said plasmid is introduced.

2. Description of the Prior Art

A human growth hormone having a molecular weight of 22,000 (hereinafter referred to as 22 kD hGH) is today used for treatment of pituitary dwarfism. Furthermore, use of the human growth hormone is expected to be expanded to, for example, the treatment of disorders such as chronic renal insufficiency in childhood, bone fractures and burns. However, 22 kD hGH is known to have side effects. As to the side effects of 22 kD hGH, it has been pointed out from the results of animal experiments that 22 kD hGH may cause leukemia when used for treatment of human patients (Rogers et al., The Lancet, 434, Aug., 27, 1977). In fact, up to 1987, the incidence of leukemia in populations who use the human growth hormone increased ten times more than anticipated, which cannot be ignored by any means (Fisher et al., The Lancet, 1159, May 21, 1988; Watanabe et al., The Lancet, 1159, May 21, 1988). As to diabetogenic activity, which is another side effect caused by 22 kD hGH, it was reported that 30% of patients who received 22 kD hGH treatment in clinical trial in Turner's syndrome showed a decrease in glucose tolerance (HORUMON TO RINSHO (Hormone and Clinical medicine), 38, 155–159, 1990). In order to develop new applications for the human growth hormone, it is strongly desired to make the human growth hormone less likely to induce side effects for practical use in the clinical field.

Besides the 22 KD hGh which is presently used, another known human growth hormone is 20 kD hGH. This 20 kD hGH is reported to have lower growth stimulating activity in a lymphoma cell line than 22 kD hGH (Endocrinol. Japon, 36(1), 9–13, 1989) and have no or reduced diabetogenic activity (Endocrinol. Japon, 34, 73–85, 1987).

Recently, it has become possible to produce the human growth hormone intracellularly, extracellularly or in the periplasm by means of recombinant DNA technology in which a gene of human growth hormone is expressed in a microorganism as a host. As to the extracellular production of 22 kD hGH, a process for the secretion and production of 22 kD hGH using *Bacillus subtilis* (Japanese Patent Laid-open No. 273591/1989) has been reported. In a 20 kD hGH production using this process for the extracellular production of 22 kD hGH, a large portion of the expressed product was intracellularlly accumulated in a precursor form that contained secretion signal of neutral protease of *Bacillus amyloliquefaciens* preceding 20 kD hGH, and is therefore different from the authentic 20 kD hGH. In this case, a small portion of 20 kD hGH expressed has been successfully secreted and accumulated at a concentration of about 1 mg/1·A660 in a culture, as a result of intensive studies on culture methods. However, the concentration of 20 kD hGH thus accumulated is not considered to be sufficient from the viewpoint of industrial production, and thus further studies are needed to increase the accumulation of 20 kD hGH. However, in this case, it is impossible to subject the culture supernatant directly to column chromatography using ordinary methods, since the medium used contained salts and polypeptides in high concentration. Thus, culture supernatant must be diluted 5–10 times prior to the column chromatography. This operation requires a big column chromatography apparatus and is disadvantageous in terms of production cost. Thus, as to the extracellular production of 20 kD hGH on an industrial scale, any satisfactory method has not yet been established.

On the other hand, as to the intracellular production of human growth hormone, Miyamoto et al. extensively studied the intracellular production of 22 kD hGH and 20 kD hGH using *E. coli* (Miyamoto et al., International Symposium on GRF, Growth Hormone and Somatomedin Program and Abstracts, 28, Nov. 1–2, 1986). With the aim of attaining the highly efficient expression of 20 kD hGH, Miyamoto et al. tried to use a method which had already been established for 22 kD hGH production to attain this highly efficient expression of 20 kD hGH. However, it was reported that the amount of 20 kD hGH expressed was only 1/10 that of 22 kD hGH. These facts suggest that 20 kD hGH cannot be effectively expressed intracellularly in *E. coli* by simply applying methods which has already been established for production of 22 kD hGH, to the 20 kD hGH production and that there are problems unique to the expression of 20 kD hGH. Namely, any satisfactory method for production of 20 kD hGH on an industrial scale has not yet been established even by intracellular production using *E. coli*, which is technically easier than production using secretion process.

As to secretion into the periplasm of *E. coli*, Gray et al. reported the secretion of 22 kD hGH (Gray et al., Gene, 39, 247–254, 1985). The periplasm refers to a space between the inner membrane and the outer membrane of gram-negative bacteria including *E. coli*. In gram-negative bacteria, a precursor protein containing a signal sequence is proceeded during secretion to cleave the secretion signal sequence that is necessary for membrane penetration upon passing through the inner membrane. The protein, which now becomes the matured protein by losing its secretion signal, generally cannot pass through the outer membrane and is accumulated in the periplasm. For secretion and accumulation of 22 kD hGH in the periplasm of *E. coli*, Gray et al. constructed a plasmid in which the 22 kD hGH gene is correctly ligated to 3'-terminal end of the region for secretion signal of *E. coli* alkaline phosphatase gene (phoA), and introduced this plasmid into *E. coli*. This report of Gray et al relates to 22 kD hGH and contains no description as to 20 kD hGH.

SUMMARY OF THE INVENTION 20 kD hGH has an amino acid sequence identical with 22 kD hGH except 15 amino acid residues are missing, which causes alteration of higher-order structure conformation. This means that application of efficient expression system for 22 kD hGH can not realize efficient production of 20 kD hGH due to conformational change.

In an intracellular expression method, a targeted protein is produced as a non-natural type containing methionine at the N-terminus and generally can not form authentic conformation. In this method, therefore, the produced protein should be correctly refolded during downstream processing.

On the other hand, in a secretion method, a targeted protein is, generally, obtained as a natural type, which is advantageous as compared to the intracellular production method; however, this method is technically difficult. Moreover, if the target product is the mammalian protein, the protein produced is susceptible to proteolysis and its secretion productivity is highly reduced due to the high-order structure. For these reasons, any effective production of a protein of animal origin using procaryotic cells has not been achieved on an industrial scale, with partial exceptions such as 22 kD hGH production.

As for 20 kD hGH, there has been no report on production in its natural-type form by secretion, even on such a low level of production that it has no industrial significance. In fact, as the present inventors show in Examples hereinafter, the amount of secretion is not satisfactory even when a secretion signal which is also used for industrial production of conventionally known 22 kD hGH is used.

An objective of the present invention is to construct a plasmid for 20 kD hGH secretion and to provide an efficient method for the production of 20 kD hGH by transforming *E. coli* cells with the said plasmid and culturing the resultant transformants so that 20 kD hGH is secreted and accumulated in the periplasm of each transformant.

As a result of extensive studies to achieve the above-mentioned objective, the present inventors found that 20 kD hGH can be efficiently secreted and accumulated in the periplasms of transformed *E. coli* cells by culturing the said transformed *E. coli* cells which are transformed with a human growth hormone secretion plasmid composed of a vector DNA and a DNA fragment in which a human growth hormone gene encoding 20 kD hGH is bound to the downstream end of the region comprising the promoter, the ribosome binding site and the secretion signal coding region which are involved in expression and secretion of the neutral protease of *Bacillus amyloliquefaciens*. Thereby the present invention was completed based on this new findings of the present inventors.

A process for the production of 20 kD hGH according to the present invention includes the steps of:

(a) preparing a 20 kD hGH secretion plasmid comprising:
  (i) a vector DNA;
  (ii) a DNA fragment comprising a promoter, a ribosome binding site and a secretion signal coding region which are those of an extracellular neutral protease gene of *Bacillus amyloliquefaciens*,
  (iii) a gene encoding mature 20 kD hGH,
  said gene encoding mature 20 kD hGH bound directly to the 3'end of the secretion signal coding region of the DNA fragment (ii) so that expression and secretion of the mature 20 kD hGH is directed by the DNA fragment (ii);

(b) transforming *E. coli* cells as host with the 20 kD hGH secretion plasmid to obtain a transformant;

(c) culturing the transformant in a suitable medium so that 20 kD hGH is secreted and accumulated in the periplasm of the transformant; and (d) recovering the 20 kD hGH from the periplasm.

According to the present invention, it has become possible that 20 kD hGH is secreted and accumulated in the periplasm. Then, 20 kD hGH can be produced in large quantities by separating and recovering the 20 kD hGH from the periplasm.

The method of the present invention is advantageous against the conventional methods using extracellular production in the following points:

20 kD hGH can be recovered as a concentrated solution of 20 kD hGH from periplasm according to the present invention, while 20 kD hGH is produced in culture medium at a very low concentration according to the methods of extracellular production.

The number of other proteins as contaminant and their amounts in the periplasm are smaller than in the culture medium.

Therefore, the subsequent purification procedure can be more simplified in the present invention than the methods using extracellular production.

BRIEF DESCRIPTION OF THE DRAWINGS

In FIG. 1, PM, SD, SS and 20 kD hGH are explained as follows:

PM: the promoter region which is necessary for expression of the neutral protease gene of *Bacillus amyloliquefaciens*.

SD: the ribosome binding site of the neutral protease gene of *Bacillus amyloliquefaciens*.

SS: the region encoding the secretion signal (secretion signal coding region) of the neutral protease gene of *Bacillus amyloliquefaciens*.

20 kD hGH: the human growth hormone gene encoding mature 20 kD hGH.

DETAILED DESCRIPTION OF THE PREFERRED EMBODIMENT

Figure 1:
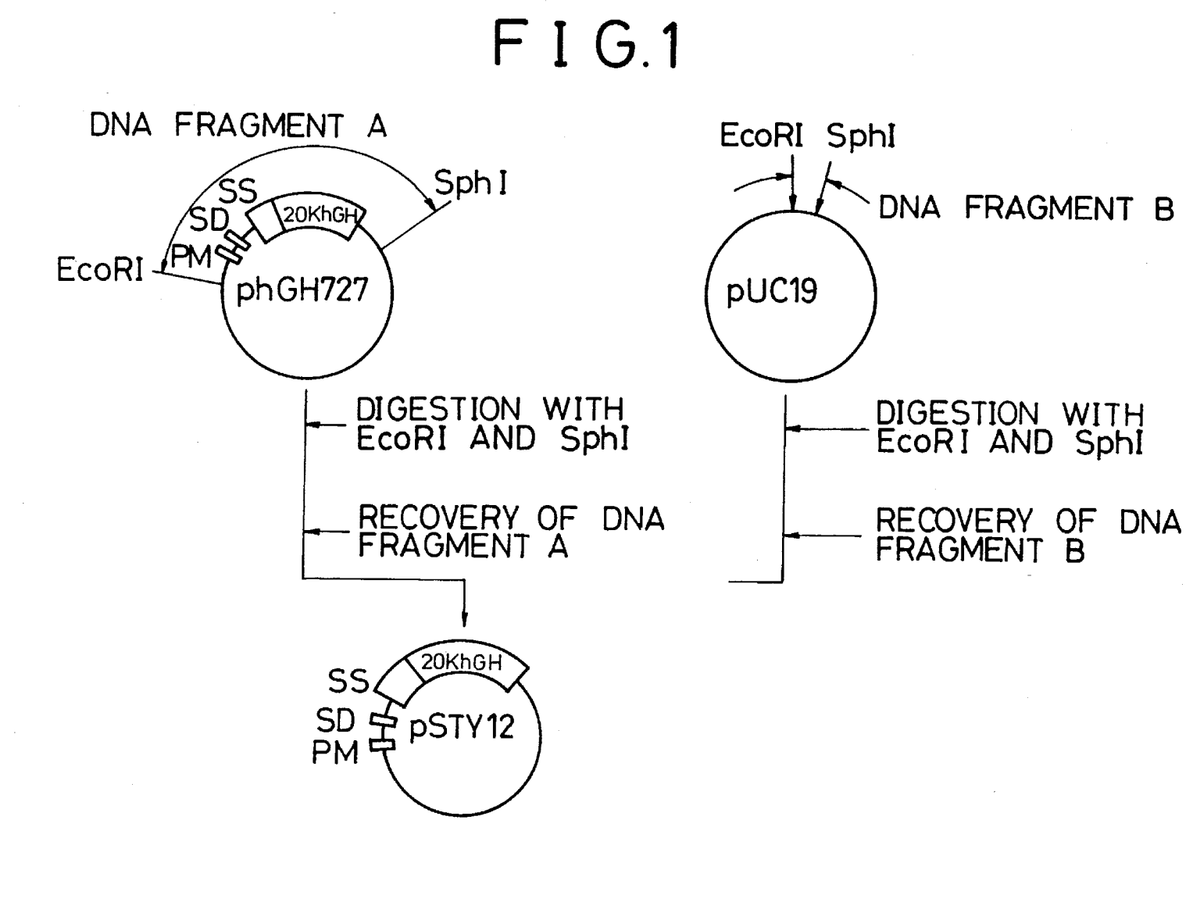
FIG. 1 illustrates a process of constructing 20 kD hGH secretion plasmid pSTY12.

The present invention is characterized in that a strain of *E. coli* selected as a host and a DNA fragment selected for 20 kD hGH secretion are combined, the DNA fragment comprising the promoter, the ribosome binding site and the secretion signal coding region, which are those of the neutral protease gene of *Bacillus amyloliquefaciens*.

The promoter comprehends a region which is recognized by and bound with RNA polymerase. In the present invention, the promoter which is involved in expression of the neutral protease gene of *Bacillus amyloliquefaciens* is used.

The ribosome binding site encodes a region of mRNA synthesized by RNA polymerase, which region is necessary for binding of the mRNA to ribosome; particularly in the present invention, the ribosome binding site of neutral protease gene of *Bacillus amyloliquefaciens* is used. These regions play an important role for gene expression. Furthermore, gene sequences of these regions are widely known to relate to the amount of gene expression. In the case where a gene encoding a targeted protein is expressed using *E. coli* as a host, *E. coli* is known to have the capability to recognize promoters and ribosome binding sites of various microorganisms other than *E. coli*.

The secretion signal comprehends a polypeptide located in N-terminal portion of the precursor protein and precedes N-terminal of a mature protein. Since this polypeptide is removed during secretion, it is considered to play an important role in extracellular transport of the secreting protein across the cell membrane (G. Blobel et al., J. Cell Biol., 67, 835, 1975). The area coding for a secretion signal in the present invention comprehends a region of the gene for the said polypeptide. Particularly in the present invention, the region of the neutral protease gene derived from *Bacillus amyloliquefaciens* is used.

The periplasm comprehends a space between the inner membrane and the outer membrane of gram-negative bacteria including *E. coli*. The secreting protein is accumulated in the periplasm. Unlike in the above-mentioned extracellular production in *Bacillus subtilis*, the protein is not released into the culture medium so that it can be recovered in a concentrated solution as periplasm fraction; furthermore, other proteins contained in the periplasm are limited in variety and small in quantity so that the purification process to follow is simplified.

As for the human growth hormone gene encoding 20 kD hGH, any known DNA fragment such as a chemically synthesized gene or cDNA based on 20 kD hGH mRNA can be used.

As for the vector DNA to construct the 20 kD hGH secretion plasmid according to the present invention, any DNA which contains a replication origin that allows the replication in E. coli can be used; for example, pBR322 and pUC19 can be used.

The promoter, the ribosome binding site, the secretion signal coding region and the gene coding for 20 kD hGH are operably bound and sequenced in this order in the direction from 5'-end to 3'-end so that expression of the precursor in which the secretion signal and 20 kD hGH are combined is directed by the promoter and the ribosome binding site. The resultant precursor is expressed and transported into the periplasm of E. coli with processing of the secretion signal during secretion.

From a practical point of view, it is possible to bind a heterologous protein gene to the downstream end (3' end) of a region which comprises a promoter, a ribosome binding site and a secretion signal coding region; moreover, in the case where a heterologous protein secretion plasmid which is replicable in E. coli is constructed, any gene which is derived from a gene of extracellular enzyme, which is produced and extracellularly secreted, can be used. Various genes are known to be useful as such an extracellular enzyme gene. However, it is not always possible that a targeted heterologous protein is sufficiently produced and secreted simply by binding a gene of a heterologous protein to the downstream end of the region which comprises the promoter, the ribosome binding site and the secretion signal of such a gene. This is evident also from Comparative Example 1. It has been first found by the present inventors that, as the promoter, the ribosome binding site and the secretion signal coding region to produce and secrete natural-type 20 kD hGH in E. coli periplasm, those derived from the neutral protease gene of Bacillus amyloliquefaciens can be used with excellent results, in combination of the 20 kD hGH gene. Then, a DNA fragment in which the human growth hormone secretion plasmid is bound immediately after the promoter, the ribosome binding site and the secretion signal derived from the said neutral protease gene is bound to a vector DNA to construct the human growth hormone.

The above-described four units (the promoter, the ribosome binding site, the secretion signal coding region and the gene encoding 20 kD hGH) are bound so as to achieve the above-mentioned objective, and the sequence either between the promoter and the ribosome binding site or between the ribosome binding site and the secretion signal coding region is not particularly restricted as long as the objective can be achieved.

The human growth hormone secretion plasmid according to the present invention can be constructed by operably linking the gene encoding 20 kD hGH to the downstream end (3' end) of the DNA fragment comprising the promoter, the ribosome binding site and the secretion signal coding region.

Two nucleotide sequences of the 20 kD hGH gene different in the 14th codon form the 5' end have been reported.

Masuda, N. et al. (Biophysica Acta, 949, 125, 1988) reported that the 14th codon of a 20 kD hGH cDNA is AGT for Ser. Martial, J. A. et al. (Science, 205, 602, 1979) reported that the 14th codon of a 20 kD hGH mRNA is AUG for Met. Therefore, examples of the DNA fragment comprising the above four units include that having SEQ ID NO: 1 or NO: 2.

The human growth hormone secretion plasmid can be constructed using a known method. Examples of the human growth hormone secretion plasmid include pSTY12 and pGHW3.

A transformed E. coli strain can be obtained by transforming E. coli using a human growth hormone secretion plasmid by an publicly-known method. A bacterial strain which can be used here may be any E. coli strain which is transformable by the 20 kD hGH secretion plasmid of the present invention; however, known E. coli strains which are not pathogenic and ubiquitously used, e.g., E. coli HB101 and W3110, can be preferably used. Thus, transformed E. coli strains which carry the human growth hormone secretion plasmid can be obtained. Examples of such strains includes MT-012 and MT-10712. These strains are deposited at the Fermentation Research Institute of the Agency of Industrial Science & Technology of the Ministry of International Trade and Industry, 1–3, Higashi 1-chome, Tsukuba-shi, Ibaraki-ken, 305, Japan, according to the Budapest Treaty. This institute's name was changed to "National Institute of Bioscience and Human-Technology" on Jan. 1, 1993. Their Accession Numbers and Deposition Dates are as follows:

| Strain Name | Deposition Date | Accession Number |
| --- | --- | --- |
| MT-012 | August 12, 1992 | FERM BP-3966 |
| MT-10712 | July 12, 1993 | FERM BP-4361 |

In order to culture E. coli transformants, a known culture method using a medium consisting of a carbon source, a nitrogen source and inorganic salts utilizable by the bacterial strains can be used; a fluid culture method is preferably used.

As to the composition of the medium, an ordinary carbon source may be used; however, in order to attain a larger amount of accumulation, in particular, glycerol is preferably used.

Namely, when bacterial cells were cultured in a 2-fold concentrated LB medium (20 g/l polypeptone, 10 g/l yeast extract) supplemented with glucose at a low concentration (0.1–0.5%) at a starting pH of 7.5 at a culture temperature of 30° C., the concentration of 20 kD hGH generally reached maximally 5–10 mg per 1 l of culture fluid; however, 20 kD hGH thereafter drastically degraded proteolytically so that the amount of accumulated 20 kD hGH decreased during a process of harvesting cells after culturing (for 1–2 hours). It is generally known that the amount of accumulation of a protein decreases after culturing, because the amount of the targeted protein accumulated decreases drastically due to proteolysis when the glucose concentration in the medium decreases due to the consumption by the bacteria in the expression of a heterologous protein of transformants (Trends in Biotechnology, 10, 310–315, 1992). Furthermore, when the bacteria were cultured under the same culture conditions as above except that the medium was supplemented with glucose at a higher concentration (more than 0.5%, in particular more than 0.7% up to 2.0%), the decrease in the amount of 20 kD hGH accumulated was less than when the lower concentration of glucose was used; however, growth was suppressed due to accumulation of organic acid(s) that causes drop of medium pH as the culture proceeded so that the maximal concentration of 20 kD hGH accumulated was reduced to 2–8 mg/l.

Other substances which can be used as a carbon source were studied in the same manner. Results showed that when glycerol was used as a carbon source at a high concentration (1.0–2.0%) under the same culture conditions, the growth suppression due to the accumulation of organic acid(s) that causes drastic pH drop was not observed and 20 kD hGH was accumulated at a concentration of about 10–20 mg/l. Furthermore, when glycerol was used at a low concentration (0.1–0.5%), drastic degradation did not occur after culturing and the amount of 20 kD hGH accumulated in the culture was maintained at a concentration of 20 mg/l or higher for more than 3 hours.

As mentioned above, when glucose or other substances are used as carbon sources, it is also possible to achieve the objective of the present invention by producing a sufficient amount of 20 kD hGH; however a special procedure is required to prevent the 20 kD hGH degradation and the growth suppression due to organic acid(s) accumulation that is derived from incomplete oxidation of glucose. Now, by adding glycerol as a carbon source to the medium, two problems, namely, the growth suppression due to accumulation of organic acid(s) causing the pH drop and the drastic degradation of the targeted protein after culturing, are solved. Therefore, glycerol can preferably be used as a carbon source to be added to the medium used for culturing according to the present invention. As to the concentration of glycerol to be added to the medium, at a concentration of less than 0.1%, the protein accumulated is markedly degraded after culturing to the same extent as in the medium without glycerol; at a concentration of 2.0% or more, cell growth is suppressed and the amount of 20 kD hGH accumulated also decreases; therefore, the addition at a concentration in a range of 0.2–2.0% is desirable.

As the components of the medium used for culturing in the present invention, polypeptone and yeast extract are used as a nitrogen source of the medium used for cultivation; each of these components can be used in a medium at an ordinary concentration (10 g/l polypeptone; 5 g/l yeast extract); however, a higher concentration is desirable because both the cell growth rate and the amount of 20 kD hGH accumulated increase as the concentration increases. However, if these compounds are added at an extremely high concentration, purification of 20 kD hGH from the culture may be disturbed; therefore, an approximately 2-fold concentrated LB medium (20 g/l polypeptone; 10 g/l yeast extract) is generally used.

In order to obtain 20 kD hGH steadily and in large quantities, the culture according to the present invention is preferably carried out at a temperature ranging from 20° to 30° C. for the following reasons. That is, when effects of temperature for culturing cells of transformed $E.\ coli$ strain according to the present invention were studied by culturing the cells using a medium supplemented with glycerol as a carbon source at various temperatures, results were unexpectedly better at 25° C. than at 30° C. in terms of cell growth rate, attainable cell concentration and amount of 20 kD hGH accumulated; the amount of 20 kD hGH accumulated in the medium cultured at 25° C. reached 30 mg/l or more. When the culture temperature was lower than 20° C., the cell growth rate was extremely slow. When the culture temperature was higher than 30° C., the cell growth was suppressed and only a small amount of 20 kD hGH was accumulated. At the temperature of 37° C., which is normally used for the growth of $E.\ coli$ cells, the bacterial cells were lysed during cultivation and reasons for such phenomena are not necessarily evident; however, it is possible that rapid synthesis of precursor 22 kD hGH at 37° C. causes intracellular accumulation of precursor protein which is toxic to host cell and induces cell death.

By culturing cells of a transformed $E.\ coli$ strain according to the present invention, 20 kD hGH is secreted and accumulated in the periplasms of the transformed cells. Preparation of 20 kD hGH from the periplasms of these $E.\ coli$ transformants can be carried out by an ordinary method of recovering and purifying proteins from the periplasm. For example, an osmotic pressure shock method (Nossal G. N., J. Biol. Chem., 241(13), 3055–3062, 1966) can be used.

Thus, a sufficient amount of 20 kD hGH can be secreted and accumulated in the periplasms of cells of a transformed $E.\ coli$ strain and the 20 kD hGH in the periplasms can be finally recovered as a preparation of the periplasm protein solution by the method according to the present invention.

The present invention will be illustrated in detail by the following examples; however, the invention is not intended to be limited to these examples. In the examples, "%" means "W/V%".

Example 1

Construction of 20 kD hGH secretion plasmid pSTY12:

A DNA fragment containing a sequence for 20 kD hGH correctly fused to 3'-terminal end of head portion of $Bacillus\ amyloliquefaciens$ neutral protease gene that contains a promoter, ribosome-binding site and secretion-signal-coding region was prepared from plasmid phGH727 which carries the DNA fragment, as follows:

A $E.\ coli$ transformant MT-600 (phGH526) carrying plasmid phGH 526 including a DNA fragment comprising the promoter, the ribosome binding site and the secretion signal coding region all of which were those of the neutral protease gene of $B.\ amyloliquefaciens$ was prepared by the method of Nakayama et al. (Biotechnol., 8, 123, 1988).

After cultivation of MT-600, plasmid phGH526 was isolated from the cultured cells by the method of Tabak et al. (Nucleic Acids Res., 5, 2321, 1978). Plasmid phGH526 was then digested with restriction endonucleases PvuII (Takara Shuzo) and BglIII (Takara Shuzo) and an about 2.4 kb DNA fragment (fragment I) and an about 5.4 kb DNA (fragment II) were isolated from the reaction mixture by agarose gel electrophoresis.

Separately, a plasmid carrying 20 kD hGH cDNA was prepared by the method disclosed in Japanese Patent Laid-Open No. 224988/1986 and digested with restriction endonucleases PvuII and BglIII and an about 0.5 kb DNA fragment (fragment III) was isolated from the reaction mixture by agarose gel electrophoresis.

Fragments I, II and III thus obtained were ligated by using the DNA ligation kit (Takara Shuzo) and thus plasmid phGH727 was constructed.

$E.\ coli$ transformant MT-727 carrying plasmid phGH727 was also deposited at the above-mentioned National Institute of Bioscience and Human-Technology of the Agency of Industrial Science & Technology on Sep. 20, 1991 under the Budapest Treaty (accession No. FERM BP-3571).

The plasmid phGH727 was prepared from the deposited strain MT-727 (FERM BP-3571) by the method of Tabak et al. (Tabak et al., Nucleic Acids Res., 5, 2321, 1978). Subsequently, the phGH727 DNA was digested with restriction endonucleases EcoRI and SphI and the resultant DNA fragment of about 2.3 Kb (hereinafter referred to as DNA fragment A) was purified by agarose gel electrophoresis.

Furthermore, pUC19 (purchased from Takara Shuzo Co., Ltd.) was used as a vector DNA which is replicable in *E. coli*. pUC19 was digested with restriction endonucleases EcoRI and SphI and a DNA fragment of 2.64 Kb (hereinafter referred to as DNA fragment B) was prepared. DNA fragment A and DNA fragment B thus prepared were ligated each using 0.01 microgram of a DNA ligation kit (a product of Takara Shuzo Co., Ltd.) to construct plasmid pSTY12 of about 4.9 Kb. This pSTY12 is a plasmid, which is replicable in E. coli, in which a region encoding matured 20 kD hGH binds immediately after the DNA fragment comprising the promoter, the ribosome binding site and the secretion signal coding region, which are those of the neutral protease gene of *Bacillus-amyloliquefaciens*.

Example 2

Construction of 20 kD hGH secretion plasmid pGHW3:

A DNA fragment of about 2.3 Kb (hereinafter referred to as DNA fragment C) was obtained by digesting phGH727 DNA with restriction endonucleases EcoRI and SphI in the same manner as described in Example 1.

Furthermore, pBR322 (purchased from Takara Shuzo Co., Ltd.) was used as a vector DNA which is replicable in *E. coli*. pBR322 was digested with restriction endonucleases EcoRI and ScaI and a DNA fragment of 3.8 Kb (hereinafter referred to as DNA fragment D) was prepared. The SpHI site of DNA fragment C and the ScaI site of DNA fragment D were made into blunt-ended fragments and the resultant fragments were ligated in the same manner as described in Example 1 to construct plasmid pGHW3 of about 5.8 Kb.

This pGHW3 is also a hybrid plasmid similar to pSTY12 described in Example 1, which is replicable in E. coli, in which a region encoding matured 20 kD hGH is bound immediately after the DNA fragment comprising the promoter, the ribosome binding site and the secretion signal coding region, which are those of the neutral protease gene of *Bacillus amyloliquefaciens*.

Example 3

Construction of natural-type 20 kD hGH:

Using the plasmid pSTY12 constructed in Example 1, cells of *E. coli* HB101 (a product of Takara Shuzo Co., Ltd.) were transformed by a known method. Thus, a transformed strain MT-012 (FERM BP-3966) was obtained. Furthermore, using the plasmid pGHW3 constructed in Example 2, cells of *E. coli* W3110 (ATCC 27325) were transformed by a known method to obtain a transformed strain MT-10712 (FERM BP-4361).

The cells of these two transformed strains were each cultured (in 20 ml of 2-fold concentrated LB medium), and the concentrations of 20 kD hGH in each fraction (a culture supernatant fraction, a periplasm fraction and an intracellular fraction) were measured by an enzyme-immunoassay using an antibody against the human growth hormone (Kato, K. et al., J. Immunol., 116, 1554, 1976). Each fraction was prepared generally according to the method of Heppel et al. (Nossal, G. N., J. Biol. Chem., 241(13), 3055–3062, 1966); exceptionally, the periplasm fraction was prepared as follows. Namely, the cultured cells were collected by centrifugation and then suspended in an isotonic solution (a 10 mM tris-HCl buffer solution (pH 7.5) containing 20% sucrose and 10 mM EDTA) in 1/10 volume of the original culture solution. The resultant suspension was allowed to stand for 30 minutes and then the cells were recovered by centrifugation. Subsequently, proteins present in the periplasms of the cells were extracted by suspending the recovered cells in chilled water of the same volume as the isotonic solution at 4° C. The suspension was centrifuged to remove cell components and the periplasm fraction was recovered. Results of the measured concentrations of 20 kD hGH were shown in Table 1. For the cultured transformants of the two strains, about 10 mg of 20 kD hGH per 1 l medium were secreted in the periplasm fraction. Since the volume of the culture solution was reduced to 1/10 during the process of preparing the periplasm fraction, the concentration of 20 kD hGH in the periplasm fraction was ten times that of culture solution; as a result, the concentration of 20 kD hGH in each periplasm fraction were 100 mg/l.

Subsequently, in order to study characteristics of 20 kD hGH which was secreted and accumulated in the periplasms, 20 kD hGH was purified from the periplasm fraction. For this purpose, the periplasm solution was applied to a DE-52 column (a product of Whatman), which had been previously equilibrated with a 10 mM Tris buffer solution (pH 7.5), and was eluted using an NaCl concentration gradient (0–0.8M).

Subsequently, the N-terminal amino acid sequence of the purified 20 kD hGH (1 nmole) was determined; it was found that this 20 kD hGH has the N-terminal amino acid sequence which is identical with that of natural-type 20 kD hGH.

Furthermore, results of analysis of the amino acid composition of the purified 20 kD hGH showed that it well agreed with the theoretical value calculated from the natural-type 20 kD hGH.

TABLE 1

| | 20 kD hGH concentration in different fractions (as calculated into mg/l culture solution) | | |
|---|---|---|---|
| | Periplasm | Culture supernatant | Intracellular fraction |
| MT-012 | 10 | 1 | 3 |
| MT-10712 | 10 | 1 | 2 |

Comparative Example 1

Construction of 20 kD hGH secretion plasmid pSTY11 and production of 20 kD hGH using *E. coli* transformed by the said plasmid:

The secretion signal coding region of the *E. coli* outer membrane protein A gene (OmpA) was synthesized based on its sequence disclosed in Movva et al. (J. Biol. Chem., 255, 27–29, 1980).

Plasmid pSTY11 was constructed by inserting into pUC19 a DNA fragment comprising the promoter and the ribosome binding site which are those of the neutral protease gene of *B. amyloliquefaciens*, the secretion signal coding region of OmpA and the 20 kD hGH cDNA placed just downstream from the secretion signal coding region of OmpA. Each components of this plasmid were operably bound for expression of a fusion protein of the *E. coli* secretion signal and 20 kD hGH and secretion of 20 kD hGH in the periplasm of *E. coli*. This plasmid is replicable in *E. coli* and has the same structure as pSTY12 except the secretion signal coding region of the neutral protease of B. amyloliquefaciens is replaced with that of OmpA.

*E. coli* cells were transformed by pSTY11 and cells of the resultant transformed strain *E. coli* HB101 (pSTY11) were cultured in the same manner as described in Example 3 to prepare an extracellular fraction, a periplasm fraction and a culture supernatant fraction; the concentration of 20 kD hGH in each fraction was measured by the enzyme-immunoassay. Results are shown in Table 2.

In comparison of Table 1 with Table 2, it is obvious that the concentration of 20 kD hGH in all fractions are larger in Table 1 than in Table 2. By this comparison, it is clearly shown that, in constructing a 20 kD hGH secretion plasmid, the secretion signal must be selected not randomly but most appropriately. Evidently, as the secretion signal to be used in this case, a region which encodes the secretion signal of the neutral protease gene of *Bacillus amyloliquefaciens* is more appropriate than a region which encodes the secretion signal of the *E. coli* outer membrane A gene (OmpA).

TABLE 2

20 kD hGH concentration in different fractions (as calculated into mg/l culture)

| Periplasm | Culture supernatant | Intracellular fraction |
|---|---|---|
| 10 | 0.3 | 0.6 |

Example 4

Cell concentration in cultures and accumulated 20 kD hGH in periplasm(s) with different carbon sources:

A series of medium solutions each containing 20 g/l polypeptone, 10 g/l yeast extract and one of the compounds shown in Table 3 (at a concentration of 0.5% or 1.5%) was prepared and the pH of the solution was adjusted to 7.5 using a 5N KOH solution. After autoclaving, sodium ampicillin was added aseptically to the solution at a concentration of 100 mg/l. Each medium (30 ml) thus prepared was inoculated with 3- platinum-loop volumes of culture of MT-012 strain and incubated at 30° C. with shaking. The cell concentration and 20 kD hGH concentration in the periplasm were monitored to determine the time to attain the maximal cell concentration, the maximal 20 kD hGH concentration and the 20 kD hGH concentration 3 hours after attaining the maximal concentration. Results are shown in Table 3.

The cell concentration was expressed by a measurement of absorbance at 660 nm and the 20 kD hGH in the periplasm was quantitatively measured by the enzyme-immunoassay of a periplasm solution which was prepared in the same manner as described in Example 3.

Using glycerol as the carbon source, growth inhibition due to accumulation of organic acid(s) that causes pH drop does not occur at high concentration (1.5%). And at low concentration (0.2%), drastic degradation of 20 kD hGH after attaining to the maximal cell concentration is not observed.

TABLE 3

Cell growth rate and accumulated 20 kD hGH concentration with different carbon sources

| Carbon source added (conc.) | Time to reach maximal cell conc. (attained conc., OD$_{660}$) | 20 kD hGH maximal conc. (mg/l culture) | 20 kD hGH conc. 3 hr after attaining maximal conc. (mg/l culture) |
|---|---|---|---|
| Sodium citrate | | | |
| (0.2%) | 6.7 hr (9.8) | 12 | 5 |
| (1.5%) | 9.5 hr (4.0) | 8 | 7 |
| Lactose | | | |
| (0.2%) | 6.0 hr (8.6) | 13 | 6 |
| (1.5%) | 9.2 hr (5.0) | 6 | 4 |

TABLE 3-continued

Cell growth rate and accumulated 20 kD hGH concentration with different carbon sources

| Carbon source added (conc.) | Time to reach maximal cell conc. (attained conc., OD$_{660}$) | 20 kD hGH maximal conc. (mg/l culture) | 20 kD hGH conc. 3 hr after attaining maximal conc. (mg/l culture) |
|---|---|---|---|
| Glucose | | | |
| (0.2%) | 6.9 hr (8.9) | 14 | 6 |
| (1.5%) | 10.5 hr (4.1) | 8 | 7 |
| Glycerol | | | |
| (0.2%) | 6.5 hr (10.2) | 25 | 24 |
| (1.5%) | 6.3 hr (9.8) | 28 | 27 |
| Sodium succinate | | | |
| (0.2%) | 7.0 hr (9.9) | 10 | 4 |
| (1.5%) | 10.9 hr (3.8) | 8 | 6 |
| Sodium acetate | | | |
| (0.2%) | 6.0 hr (10.6) | 10 | 4 |
| (1.5%) | 8.9 hr (2.9) | 6 | 6 |

Example 5

Effect of culture temperature on attainable maximal cell concentration and accumulated 20 kD hGH concentration:

A solution containing 20 g/l polypeptone, 10 g/l yeast extract and 0.5% glycerol was prepared and the pH of the solution was adjusted to 7.5 using a 5N KOH solution. After autoclaving, sodium ampicillin was added aseptically to the solution at a concentration of 100 mg/l. The medium thus prepared (30 ml) was inoculated with 3-platinum-loop volumes of cell culture of MT-012 strain and incubated with shaking at temperatures indicated in Table 4. The cell concentration and 20 kD hGH concentration in the periplasm at each temperature were monitored to determine the time to attain the maximal cell concentration and the maximal 20 kD hGH concentration. Results are shown in Table 4.

The cell concentration was expressed by a measurement of absorbance at 660 nm and 20 kD hGH in the periplasm was quantitatively measured by the enzyme-immunoassay of a periplasm solution which was prepared in the same manner as described in Example 3.

Cell growth was slow when the culture temperature was 20° C. and almost no growth was observed when the culture temperature was 35° C.

TABLE 4

Cell growth rate and accumulated 20 kD hGH concentration with different culture temperatures

| Culture temperature (°C.) | Time to reach maximal cell concentration | Maximal cell conc. attainable (OD$_{660}$) | Maximal conc. of 20 kD hGH accumulated (mg/l culture) |
|---|---|---|---|
| 20° C. | 13.5 hr | 6.8 | 10.2 |
| 25° C. | 5.0 hr | 11.0 | 32.0 |
| 30° C. | 6.5 hr | 9.2 | 21.0 |
| 35° C. | Almost no growth | — | — |

5,496,713

What is claimed is:

1. A method for producing 20 kD human growth hormone which comprises the steps of:
   (a) preparing a recombinant plasmid comprising:
      i. a vector DNA replicable in Escherichia coli;
      ii. a DNA fragment comprising a promoter region, a ribosome binding site and a secretion signal coding region, said site and regions being those of the neutral protease gene of *Bacillus amyloliquefaciens*; and
      iii. a gene encoding the 20 kD hGH bound to the 3' end of the secretion signal coding region, so that expression and secretion of the 20 kD hGH is directed by the DNA fragment (ii);
   (b) transforming *E. coli* cells with the recombinant plasmid to obtain a transformant carrying the recombinant plasmid;
   (c) culturing the transformant thus obtained at a temperature between 20° to 30° C. to produce the 20 kD hGH in the periplasm of the transformant; and
   (d) recovering the 20 kD hGH from the periplasm.

2. A method according to claim 1, wherein the transformant is cultured in a culture medium containing glycerol at a concentration between 0.1 and 2%.

3. A method according to claim 1 or 2, wherein the DNA fragment has the nucleotide sequence of SEQ ID NO: 1.

4. A method according to claim 1 or 2, wherein the DNA fragment has the nucleotide sequence of SEQ ID NO: 2.

* * * * *